(12) United States Patent
Benicewicz et al.

(10) Patent No.: US 10,934,395 B2
(45) Date of Patent: Mar. 2, 2021

(54) POLYBENZIMIDAZOLE OLIGOMERS WITH REACTIVE END GROUPS

(71) Applicant: PBI Performance Products, Inc., Charlotte, NC (US)

(72) Inventors: Brian C. Benicewicz, Columbia, SC (US); Amin Daryaei, Indianapolis, IN (US); Ran Liu, Alpharetta, GA (US); Gregory S. Copeland, Tega Cay, SC (US)

(73) Assignee: PBI PERFORMANCE PRODUCTS, INC., Charlotte, NC (US)

( * ) Notice: Subject to any disclaimer, the term of this patent is extended or adjusted under 35 U.S.C. 154(b) by 22 days.

(21) Appl. No.: 16/432,994

(22) Filed: Jun. 6, 2019

(65) Prior Publication Data

US 2019/0382531 A1   Dec. 19, 2019

Related U.S. Application Data

(60) Provisional application No. 62/685,315, filed on Jun. 15, 2018.

(51) Int. Cl.
  *C08G 73/18* (2006.01)
  *C07D 235/18* (2006.01)

(52) U.S. Cl.
  CPC .......... *C08G 73/18* (2013.01); *C07D 235/18* (2013.01)

(58) Field of Classification Search
  USPC ........................................ 528/271, 272, 289
  See application file for complete search history.

(56) References Cited

U.S. PATENT DOCUMENTS

| | | | |
|---|---|---|---|
| 3,969,430 A * | 7/1976 | Kalnin | C08J 5/00 525/435 |
| 4,912,176 A | 3/1990 | Alvarez et al. | |
| 5,089,568 A | 2/1992 | Harris et al. | |
| 9,598,541 B2 | 3/2017 | Benicewicz et al. | |
| 2009/0004508 A1 | 1/2009 | Funaki et al. | |
| 2011/0189581 A1 | 8/2011 | Choi et al. | |
| 2012/0219879 A1 | 8/2012 | Hu et al. | |

OTHER PUBLICATIONS

Chengji Zhao et al. "Covalently cross-linked proton exchange membranes based on sulfonated poly(arylene ether ketone) and polybenzimidazole oligomer" Journal of Membrane Science; vol. 353, Issues 1-2, May 1, 2010, pp. 10-16. (Year: 2010).*
Kayley Fishel et al., "PBI Membranes Via the PPA Process," Springer International Publishing (Switzerland), (p. 217-238), (2016).

* cited by examiner

*Primary Examiner* — Terressa Boykin
(74) *Attorney, Agent, or Firm* — Hammer & Associates, P.C.

(57) ABSTRACT

A polybenzimidazole (PBI) resin including a polybenzimidazole oligomer having at least two reactive end groups is provided. Also provided is a method of making a polybenzimidazole oligomer with at least two reactive end groups including the steps of reacting a tetraamine, a dicarboxylic component, and a reactive end group moiety in a solvent at a temperature greater than room temperature for a period of time; precipitating the oligomer from the solvent after reacting; and removing any reaction by-products from the oligomer after precipitating. A method of making a PBI molded article and a PBI molded article are also provided.

12 Claims, No Drawings

POLYBENZIMIDAZOLE OLIGOMERS WITH REACTIVE END GROUPS

CROSS REFERENCE TO RELATED APPLICATIONS

The instant application claims the benefit of U.S. Provisional Patent Application Ser. No. 62/685,315, filed Jun. 15, 2018.

FIELD OF THE INVENTION

The invention relates to polybenzimidazole (PBI) resins, specifically PBI resins with reactive end groups, a method of making a PBI resin, a method of making molded articles from a PBI resins and PBI resin molded articles.

BACKGROUND OF THE INVENTION

There is a need for a new polybenzimidazole (PBI) resin that is moldable or extrudable, but still has the commercially desirable tensile, thermal, oxidative, and chemical-resistant properties of the currently commercial PBI resins.

SUMMARY OF THE INVENTION

In a first embodiment the invention provides a polybenzimidazole (PBI) resin which includes a PBI oligomer having at least two reactive end groups. The resin is moldable into articles and exhibits desirable mechanical and tensile properties. The resin is made by reacting a tetraamine, a dicarboxylic component, and a reactive end group moiety in a solvent at a temperature greater than room temperature for a period of time; precipitating the oligomer from the solvent after reacting; and removing any reaction by-products from the oligomer after precipitating.

In one embodiment, the PBI resin further comprises one or more additives selected from the group consisting of fillers, flame retardants, flame retardant aids, plasticizers, antioxidants, releasing agents, light fastness agents, weathering agents, colorants, pigments, modifiers, antistatic agents, hydrolysis inhibitors, and reinforcing agents. In an alternative embodiment, one or more additives are added along with the PBI resin during the molding process. Additives added along with the PBI during molding may include fillers, flame retardants, flame retardant aids, plasticizers, antioxidants, releasing agents, light fastness agents, weathering agents, colorants, pigments, modifiers, antistatic agents, hydrolysis inhibitors, processing aids, flow control agents, and reinforcing agents.

DESCRIPTION OF THE INVENTION

A polybenzimidazole (PBI) resin (or polymer) generally includes a polybenzimidazole oligomer with at least two reactive end groups. The oligomer generally has a molecular weight in the range of: (a) about 0.015-0.60 dL/g (IV per procedure below) or (b) about 1000 to 15,000 Daltons (Da). The PBI oligomer may be the reaction product of a tetraamine, a dicarboxylic component, and a reactive end group moiety.

The molecular weight of the PBI oligomer may be any molecular weight less than the molecular weight of the PBI polymer. In some embodiments, the molecular weight may be, as measured in IV (see procedure below), in a range of about 0.015-0.60 dL/g, or about 0.020-0.55 dL/g, or about 0.030-0.50 dL/g, or any subset there included. In some embodiments, the molecular weight may be in a range of about 1,000-15,000 Daltons (Da), or any subset there included.

PBI oligomers may be the reaction products of: a tetraamine, a dicarboxylic component (e.g., dicarboxylic acids and/or the esters of such acids), and a reactive end group moiety. The following generalized equation illustrates the condensation reaction which occurs in forming the PBI oligomers:

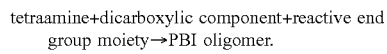

tetraamine+dicarboxylic component+reactive end group moiety→PBI oligomer.

Alternatively, the PBI oligomer may be made by the aldehyde adduct (or aldehyde bisulfite) process described in U.S. Pat. No. 9,598,541, incorporated herein by reference. The aldehyde adduct method includes the step of: reacting, in a solution. A solvent may be selected from the group of: N, N-dimethylacetamide (DMAc), N, N-dimethylformamide (DMF), dimethylsulfoxide (DMSO), N-methyl-2-pyrrolidone (NMP), tetramethylene sulfone, and combinations thereof. The organic aldehyde adduct may be an organic aldehyde bisulfite adduct. The organic aldehyde portion of the organic aldehyde adduct being aliphatic, alicyclic, aromatic, heterocyclic, or heteroaromatic or mixtures thereof. Alternatively, the AB-PBI method may be used, see K. Fishel, et al., *PBI Membranes via the PPA Process*, Springer International Publishing, Switzerland, 2016, incorporated herein by reference. The AB-PBI polymer consists of a repeat unit of a 2,5-benzimidazole ring and is synthesized using 3,4-diaminobenzoic acid.

The tetraamine may be any tetraamine. Hereinafter, tetraamine will be described as an aromatic tetraamine, but the tetraamine is not so limited. Aromatic tetraamines which may be used, for example, are those with the following formulas:

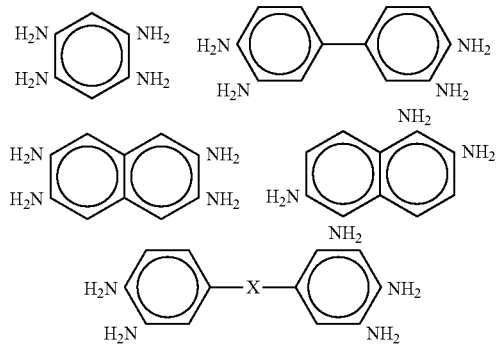

where X represents —O—, —S—, —SO$_2$, —C—, —C(CF$_3$)—, or a lower alkylene group, such as —CH$_2$—, —(CH$_2$)$_2$—, or —C(CH$_3$)$_2$—. Among such aromatic tetraamines may be mentioned, for example, 1,2,4,5-tetraaminobenzene; 1,2,5,6-tetraaminonaphthalene; 2,3,6,7-tetraaminonaphthalene; 3,3',4,4'-tetraaminodiphenyl methane; 3,3',4,4'-teraaminodiphenyl ethane; 3,3',4,4'-tetraaminodiphenyl-2,2-propane; 3,3',4,4'-tetraaminodiphenyl thioether; and 3,3',4,4'-tetraaminodiphenyl sulfone. The preferred aromatic tetraamine is 3,3',4,4'-tetraaminobiphenyl.

The dicarboxylic component (e.g., dicarboxylic acids and/or the esters of such acids) may be illustrated by the formula:

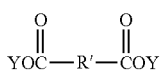

in which the Y's may be hydrogen, aryl or alkyl and the OY may be a halide. The dicarboxylic component may therefore consist of a mixture of a free acid with at least at one diester and/or monoester; a mixture of diester(s) and/or monoester(s); or a single dialkyl ester, monoester or mixed aryl-alkyl or alkyl/alkyl ester but can consist completely of free acid or diphenyl ester. When Y is alkyl, it preferably contains 1 to 5 carbon atoms and is most preferably methyl. When Y is aryl, it may be any monovalent aromatic group obtained by filling with hydrogen all the valences but one of the aromatic groups which may be R or R' as disclosed previously, either unsubstituted or substituted with any inert monovalent radical such as alkyl or alkoxy containing 1 to 5 carbon atoms. Examples of such aryl groups are phenyl, naphthyl, the three possible phenylphenyl radicals and the three possible tolyl radicals. The preferred aryl group is usually phenyl. The dicarboxylic acids, free or esterified form as part of the dicarboxylic component, may include aromatic dicarboxylic acids; aliphatic dicarboxylic acids (preferably, those having 4 to 8 carbon atoms); and heterocyclic dicarboxylic acids wherein the carboxylic groups are substituents upon carbon atoms in a ring compound such as pyridine, pyrazine, furan, quinoline, thiophene, and pyran. Dicarboxylic acids, free or esterified form, may be aromatic dicarboxylic acids such as those illustrated below:

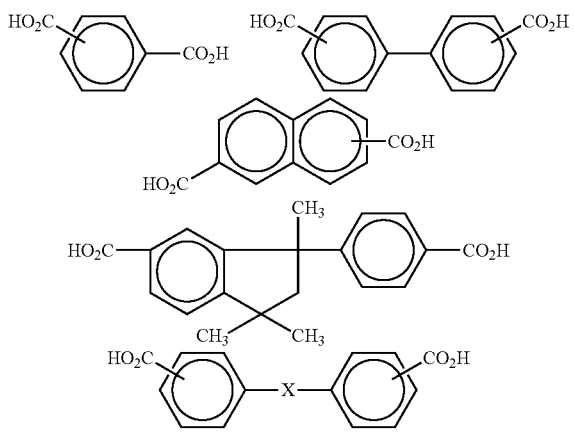

where X is as defined above. For example, the following diacids can suitably be employed: isophthalic acid; terephthalic acid; 4,4'-biphenydicarboxylic acid; 1,4-naphthalenedicarboxylic acid; diphenic acid (2,2'-biphenyldicarboxylic acid); phenylindandicarboxylic acid; 1,6-napthalenedicarboxylic acid; 2,6-naphthalenedicarboxylic acid; 4,4'-diphenyletherdicarboxylic acid; 4,4'-diphenylsulfonedicarboxylic acid; 4,4'-diphenylthioetherdicarboxylic acid. The dicarboxylic component may be one of the following combinations: (1) at least one free dicarboxylic acid and at least one diphenyl ester of a dicarboxylic acid; (2) at least one free dicarboxylic acid and at least one dialkyl ester of a dicarboxylic acid, and (3) at least one diphenyl ester of a dicarboxylic acid and at least one dialkyl ester of a dicarboxylic; and (4) at least one dialkyl ester of a dicarboxylic acid. The dicarboxylic moieties of the compounds of each combination may be the same or different and the alkyl groups of the alkyl esters of combinations (2), (3) and (4) generally contain 1 to 5 carbon atoms and are most preferably methyl. The dicarboxylic component can be employed in a ratio of about 1 mole of total dicarboxylic component per mole or aromatic tetraamine. However, the optimal ratio of reactants in a particular polymerization system can be easily determined by one of ordinary skill in the art.

The reactive end group moiety is any moiety that will facilitate cross-linking of the oligomers at temperatures under about 250° C. and, in some embodiments eliminate the concern of off-gassing or by-product (e.g. salt by-product) production when cross-linking. These moieties may be, for example, moieties with alkynyl groups (A, C below, meta shown, but includes para) and/or cyclobutane groups (B below):

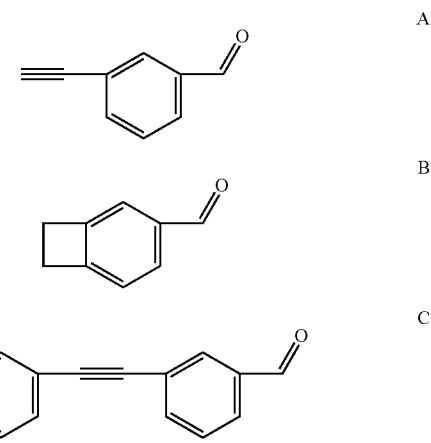

In some embodiments, the reactive end group moieties may be, for example:

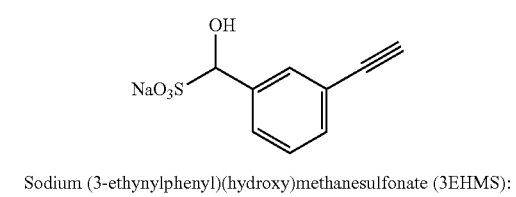

Sodium (3-ethynylphenyl)(hydroxy)methanesulfonate (3EHMS):

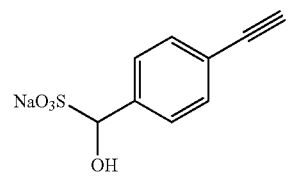

Sodium (4-ethynylphenyl)(hydroxy)methanesulfonate (4EHMS):

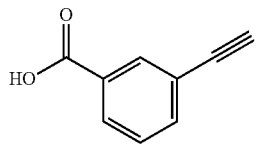

3-Ethynylbenzoic acid (3-EBA):

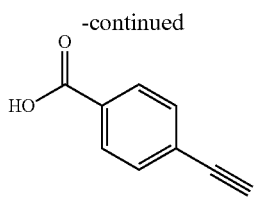

4-Ethynylbenzoic acid (4-EBA):

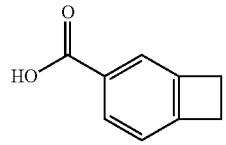

Benzocyclobutane-4-carboxylic acid (BCB):.

The solvent for the reaction may include: N, N-dimethylacetamide (DMAc), N, N-dimethylformamide (DMF), dimethylsulfoxide (DMSO), N-methyl-2-pyrrolidone (NMP), tetramethylene sulfone, polyphosphoric acid (PPA), and combinations thereof.

The reaction is conducted at a temperature greater than room temperature for a period of time. The temperature is less than the temperature to initiate cross-linking of the reactive end groups. In one embodiment, the temperature may be in a range of 150-175° C. or 160-165° C., and the period of time may be 30-70 hours or 40-60 hours or about 48 hours. In another embodiment, the reaction may be conducted as follows: at 50° C. for 1 hour, 120° C. for 6 hours, 170° C. for 10 hours, and 190° C. for 2 hours.

After completion of the reaction, the oligomer is precipitated in deionized water and washed. In some embodiments the precipitate is further washed and/or neutralized as needed.

The oligomer may be molded or extruded into shapes or articles and cured at a temperature and pressure sufficient to facilitate cross-linking of the reactive end groups. In general, oligomer shaped into pellets but not cured could be crumbled with hand pressure. After curing, those pellets would not crumble with hand pressure. In one embodiment, the PBI resin further comprises one or more additives selected from the group consisting of fillers, flame retardants, flame retardant aids, plasticizers, antioxidants, releasing agents, light fastness agents, weathering agents, colorants, pigments, modifiers, antistatic agents, hydrolysis inhibitors, and reinforcing agents. In an alternative embodiment, one or more additives are added along with the PBI resin during the molding process. Additives added along with the PBI during molding may include fillers, flame retardants, flame retardant aids, plasticizers, antioxidants, releasing agents, light fastness agents, weathering agents, colorants, pigments, modifiers, antistatic agents, hydrolysis inhibitors, processing aids, flow control agents, and reinforcing agents. Curing of the pellets may be under the following conditions: oligomer molecular weight ranges of: IV—0.015-0.60 dL/g, and/or 1000-15000 Dalton, and/or all subsets thereof; molding temperatures—120-250° C., and/or 130-200° C., and/or 135-160° C., and all subsets thereof; and molding pressures—15-150 kpsi [100-1000 kilopascal], and/or 20-130 kpsi [135-900 kilopascal], and/or 25-120 kpsi [170-830 kilopascal], and all subsets thereof; and any and all combinations of the above mentioned conditions.

INVENTIVE EXAMPLES

Oligomer Synthesis

Synthesis Example ("Syn. Ex.") 1

Synthesis of ethynyl terminated m-PBI oligomer with targeted molecular weight of 3,000 Da.

An ethynyl terminated m-PBI oligomer with a targeted molecular weight of 3,000 Da (DP=9) was synthesized as follows: TAB (10 mmol, 2.1427 g), IBA (8.86 mmol, 3.034 g), 3EHMS (2.27 mmol, 0.532 g), and DMAc (or N, N'-dimethylacetamide) (28 mL) were charged into a 150-mL three neck round bottom flask equipped with a mechanical stirrer, condenser, nitrogen inlet, and Dean-Stark trap. The mixture was stirred in an oil bath at 160-165° C. for 48 h to complete polymerization. The resulting solution was precipitated in DI water (500 ml) and stirred for 30 min. The precipitate was filtered and then stirred in boiling DI water (500 ml) for 4 hours. The last step was repeated one more time to dissolve any residual salts. Once filtered, the solid powder was dried under reduced pressure in vacuum oven at 120° C. for 12 h. IV ($H_2SO_4$ at 23° C.)=0.24 dL/g.

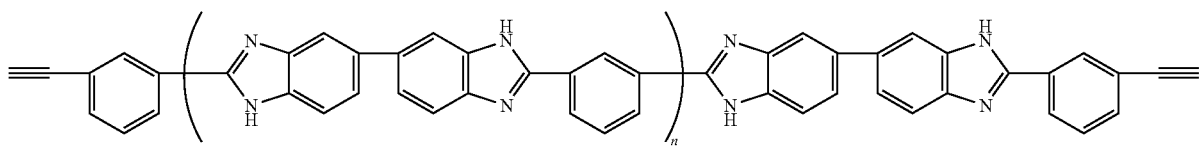

Ethynyl terminated m-PBI oligomer:

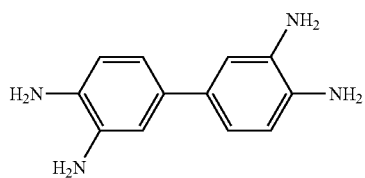

[1,1'-biphenyl]-3,3',4,4'-tetraamine (TAB):

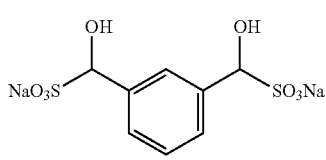

Sodium 1,3-phenylenebis(hydroxymethanesulfonate) (IBA):

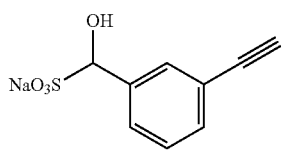

Sodium (3-ethynylphenyl)(hydroxy)methanesulfonate (3EHMS):

Synthesis Example 2

Synthesis of ethynyl terminated m-PBI oligomer with targeted molecular weight of 5,000 Da.

An ethynyl terminated m-PBI oligomer with a molecular weight of 5,000 Da (DP=15) was synthesized as follows. TAB (10 mmol, 2.1427 g), IBA (9.35 mmol, 3.2 g), 3EHMS (1.31 mmol, 0.306 g), and DMAc (28 mL) were charged into a 150-mL three neck round bottom flask equipped with a mechanical stirrer, condenser, nitrogen inlet, and Dean-Stark trap. The mixture was stirred in an oil bath at 160-165° C. for 48 h to complete polymerization. The resulting solution was precipitated in DI water (500 ml) and stirred for 30 min. The precipitate was filtered and then stirred in boiling DI water (500 ml) for 4 hours. The last step was repeated one more time to dissolve any residual salts. Once filtered, the solid powder was dried under reduced pressure in vacuum oven at 120° C. for 12 h. IV ($H_2SO_4$ at 23° C.)=0.37 dL/g.

Synthesis Example 3

Synthesis of ethynyl terminated m-PBI oligomer with targeted molecular weight of 7,000 Da.

An ethynyl terminated m-PBI oligomer with a molecular weight of 7,000 Da (DP=22) was synthesized as follows. TAB (10 mmol, 2.1427 g), IBA (9.54 mmol, 3.265 g), 3EHMS (0.92 mmol, 0.215 g), and DMAc (28 mL) were charged into a 150-mL three neck round bottom flask equipped with a mechanical stirrer, condenser, nitrogen inlet, and Dean-Stark trap. The mixture was stirred in an oil bath at 160-165° C. for 48 h to complete polymerization. The resulting solution was precipitated in DI water (500 ml) and stirred for 30 min. The precipitate was filtered and then stirred in boiling DI water (500 ml) for 4 hours. The last step was repeated one more time to dissolve any residual salts. Once filtered, the solid powder was dried under reduced pressure in vacuum oven at 120° C. for 12 h. IV ($H_2SO_4$ at 23° C.)=0.44 dL/g. A second run was run under identical conditions and produced a similar powder, IV ($H_2SO_4$ at 23° C.)=0.46 dL/g.

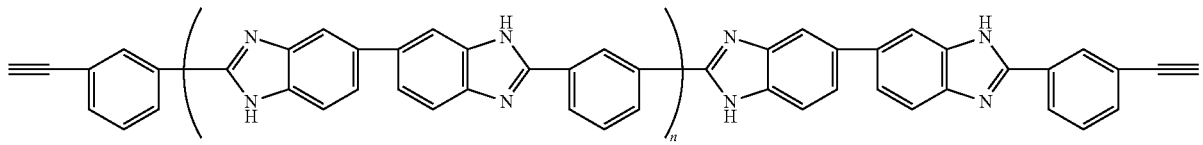

Ethynyl terminated m-PBI oligomer:

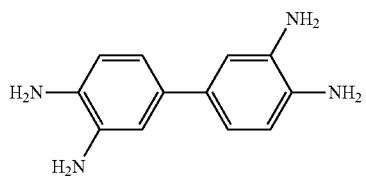

[1,1'-biphenyl]-3,3',4,4'-tetraamine (TAB):

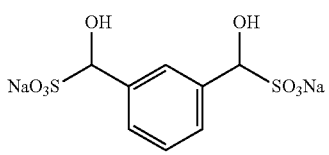

Sodium 1,3-phenylenebis(hydroxymethanesulfonate) (IBA):

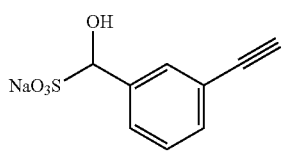

Sodium (3-ethynylphenyl)(hydroxy)methanesulfonate (3EHMS):

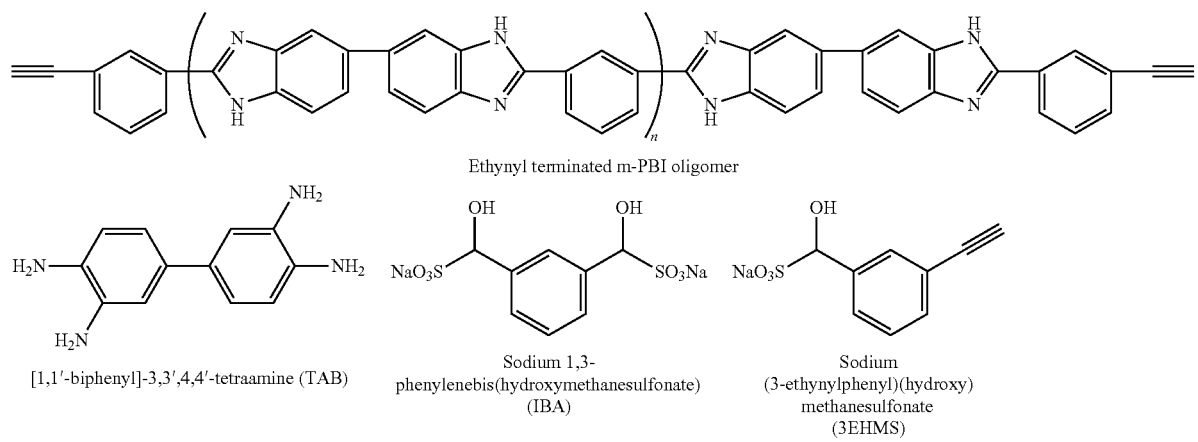

Synthesis Example 4

Synthesis of ethynyl terminated m-PBI oligomer with targeted molecular weight of 10,000 Da.

An ethynyl terminated m-PBI oligomer with a targeted molecular weight of 10,000 Da (DP=31) was synthesized as follows: TAB (10 mmol, 2.1427 g), IBA (9.97 mmol, 3.314 g), 3EHMS (0.63 mmol, 0.1485 g), and DMAc (28 mL) were charged into a 150-mL three neck round bottom flask equipped with a mechanical stirrer, condenser, nitrogen inlet, and Dean-Stark trap. The mixture was stirred in an oil bath at 160-165° C. for 48 h to complete polymerization. The resulting solution was precipitated in DI water (500 ml) and stirred for 30 min. The precipitate was filtered and then stirred in boiling DI water (500 ml) for 4 hours. The last step was repeated one more time to dissolve any residual salts. Once filtered, the solid powder was dried under reduced pressure in vacuum oven at 120° C. for 12 h. IV ($H_2SO_4$ at 23° C.)=0.51 dL/g.

Synthesis Example 5

Synthesis of ethynyl terminated STAB-based oligomer with targeted molecular weight of 1,200 Da.

An ethynyl terminated m-PBI oligomer with a targeted molecular weight of 1,200 Da (DP=2) was synthesized as follows: STAB (10 mmol, 2.7833 g), IPA (5.8 mmol, 0.964 g), 3EBA (6.6 mmol, 0.97 g), and PPA, or polyphosphoric acid, (60 g) were charged into a 150-mL three neck cylindrical kettle flask equipped with a mechanical stirrer, nitrogen inlet, and nitrogen outlet. The mixture was stirred in an oil bath at 50° C. for 1 h, 120° C. for 6 h, and 170° C. for 10 h, and 190° C. for 2 h to complete polymerization. The resulting solution was precipitated in DI water (500 ml) and blended with a blender for 15 min to make fine powder. The precipitate was filtered and then stirred in DI water (500 ml) for 2 hours. Ammonium hydroxide was added to the solution to neutralize the solution. The neutralized solution was filtered, and the solid powder was stirred in boiling DI water (500 ml) for an extra 2 hours to dissolve produced salt. The last step was repeated one more time to dissolve any residual salts. Once filtered, the solid powder was dried under reduced pressure in vacuum oven at 120° C. for 12 h. IV ($H_2SO_4$ at 23° C.)=0.20 dL/g.

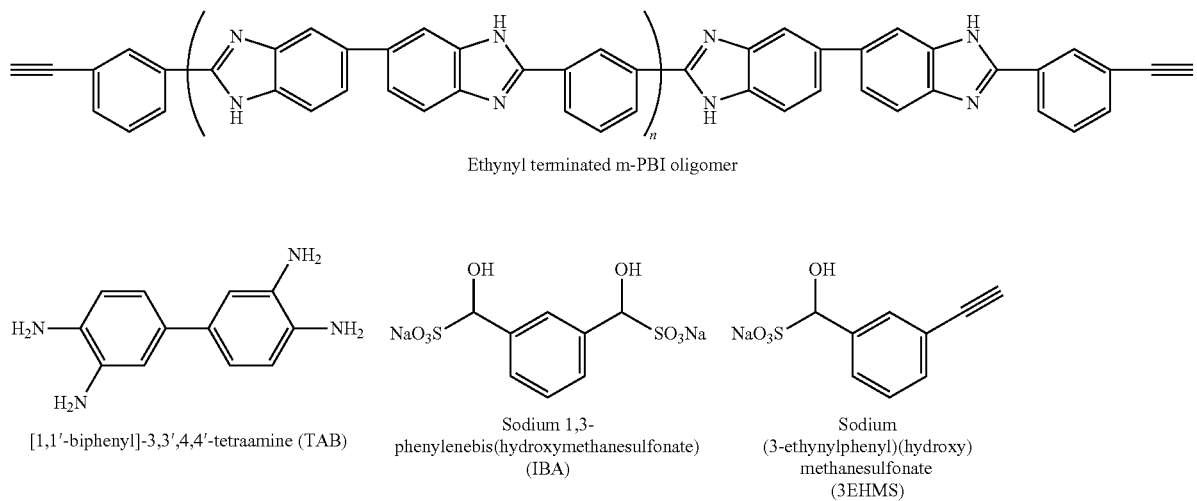

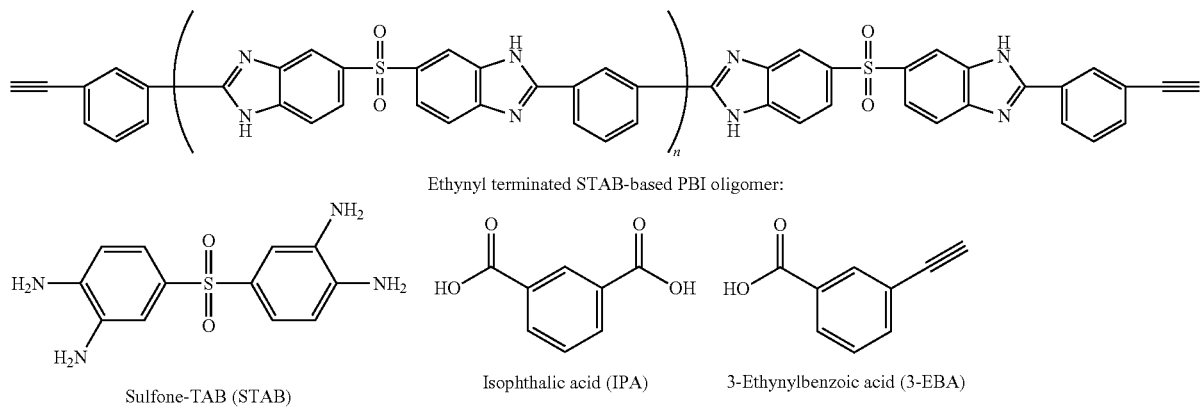

Ethynyl terminated STAB-based PBI oligomer:

Sulfone-TAB (STAB)    Isophthalic acid (IPA)    3-Ethynylbenzoic acid (3-EBA)

Synthesis Example 6

Synthesis of ethynyl terminated Sulfone-TAB-based (STAB) oligomer with targeted molecular weight of 5,000 Da.

An ethynyl terminated m-PBI oligomer with a targeted molecular weight of 5,000 Da (DP=13) was synthesized as follows: STAB (10 mmol, 2.7833 g), IPA (9.2 mmol, 1.53 g), 3EBA (1.5 mmol, 0.223 g), and PPA (57 g) were charged into a 150-mL three neck cylindrical kettle flask equipped with a mechanical stirrer, nitrogen inlet, and nitrogen outlet. The mixture was stirred in an oil bath at 50° C. for 1 h, 120° C. for 6 h, and 170° C. for 10 h, and 190° C. for 2 h to complete polymerization. The resulting solution was precipitated in DI water (500 ml) and blended with a blender for 15 min to make fine powder. The precipitate was filtered and then stirred in DI water (500 ml) for 2 hours. Ammonium hydroxide was added to the solution to neutralize the solution. The neutralized solution was filtered, and the solid powder was stirred in boiling DI water (500 ml) for an extra 2 hours to dissolve produced salt. The last step was repeated one more time to dissolve any residual salts. Once filtered, the solid powder was dried under reduced pressure in vacuum oven at 120° C. for 12 h. IV ($H_2SO_4$ at 23° C.)=0.31 dL/g.

Synthesis Example 7

Synthesis of ethynyl terminated Sulfone-TAB-based (STAB) oligomer with targeted molecular weight of 2,000 Da.

A STAB-6FBPA ethynyl terminated oligomer with a targeted molecular weight of 2,000 Da (DP=3) was synthesized as follows: STAB (5 mmol, 1.391 g), 6FBA (3.3 mmol, 1.3 g), 3EBA (2.77 mmol, 0.4 g), and PPA (103 g) were charged into a 150-mL three neck cylindrical kettle flask equipped with a mechanical stirrer, nitrogen inlet, and nitrogen outlet. The mixture was stirred in an oil bath at 50° C. for 1 h, 120° C. for 6 h, and 170° C. for 10 h, and 190° C. for 2 h to complete polymerization. The resulting solution was precipitated in DI water (500 ml) and blended with a blender for 15 min to make fine powder. The precipitate was filtered and then stirred in DI water (500 ml) for 2 hours. Ammonium hydroxide was added to the solution to neutralize the solution. The neutralized solution was filtered, and the solid powder was stirred in boiling DI water (500 ml) for an extra 2 hours to dissolve produced salt. The last step was repeated one more time to dissolve any residual salts. Once filtered, the solid powder was dried under reduced pressure in vacuum oven at 120° C. for 12 h. IV ($H_2SO_4$ at 23° C.)=0.39 dL/g.

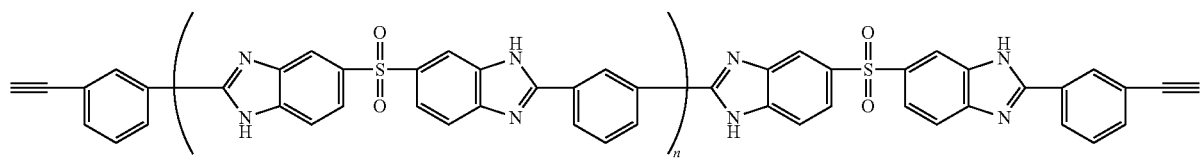

Ethynyl terminated STAB-based PBI oligomer:

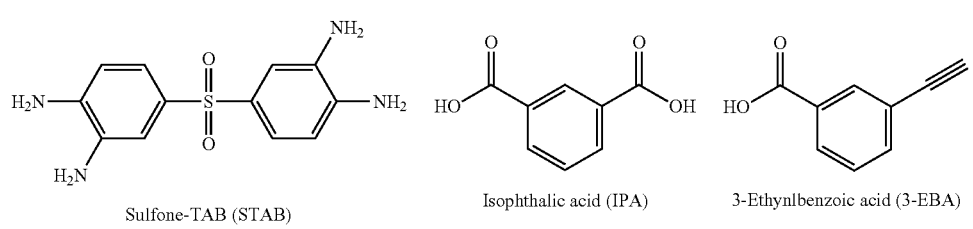

Sulfone-TAB (STAB)    Isophthalic acid (IPA)    3-Ethynlbenzoic acid (3-EBA)

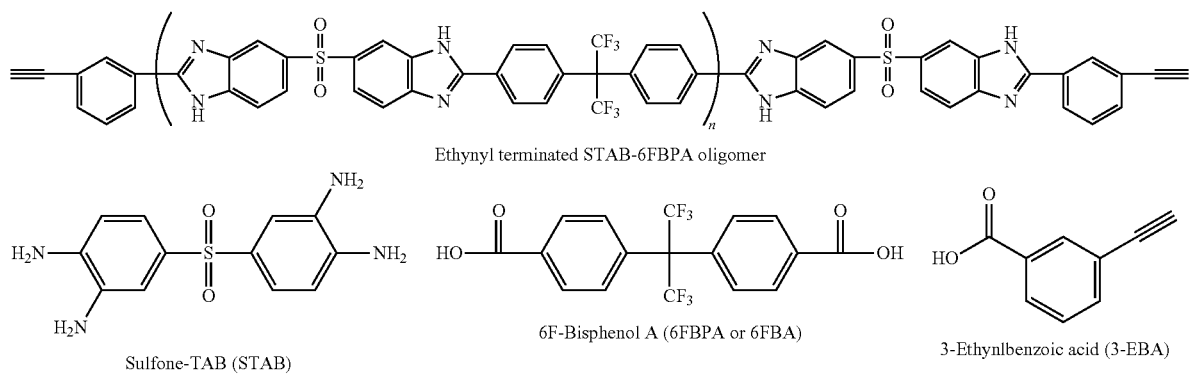

Ethynyl terminated STAB-6FBPA oligomer

Sulfone-TAB (STAB)

6F-Bisphenol A (6FBPA or 6FBA)

3-Ethynlbenzoic acid (3-EBA)

Synthesis Example 8

Synthesis of ethynyl terminated Sulfone-TAB-based (STAB) oligomer with targeted molecular weight of 4,000 Da.

A STAB-6FBPA ethynyl terminated oligomer with a targeted molecular weight of 4,000 Da (DP=6) was synthesized as follows: STAB (5 mmol, 1.391 g), 6FBA (4.2 mmol, 1.65 g), 3EBA (1.5 mmol, 0.215 g), and PPA (108 g) were charged into a 150-mL three neck cylindrical kettle flask equipped with a mechanical stirrer, nitrogen inlet, and nitrogen outlet. The mixture was stirred in an oil bath at 50° C. for 1 h, 120° C. for 6 h, and 170° C. for 10 h, and 190° C. for 2 h to complete polymerization. The resulting solution was precipitated in DI water (500 ml) and blended with a blender for 15 min to make fine powder. The precipitate was filtered and then stirred in DI water (500 ml) for 2 hours. Ammonium hydroxide was added to the solution to neutralize the solution. The neutralized solution was filtered, and the solid powder was stirred in boiling DI water (500 ml) for an extra 2 hours to dissolve produced salt. The last step was repeated one more time to dissolve any residual salts. Once filtered, the solid powder was dried under reduced pressure in vacuum oven at 120° C. for 12 h. IV ($H_2SO_4$ at 23° C.)=0.46 dL/g.

Pellet Preparation, Curing Studies, and Solubility Tests:

Pellets of samples with the size of 0.5 and 0.78" in diameter were prepared under a variety of conditions (temperature 135-190° C. and pressures of 25-120 kpsi [170-830 kilopascal]) using a hydraulic compressor. Investigation of pellet preparation resulted in products with colors ranging from pale brown to dark brown colors. Preparation of pellets at temperatures ~150-160° C. and pressures of 25-60 kpsi [170-415 kilopascal] for ethynyl terminated m-PBI terminated oligomers resulted in homogeneous and uniformly fused samples with a shiny and smooth surface. The same result was observed for STAB-based oligomers at temperatures 135-160° C. and pressures of 25-30 kpsi [170-207.5 kilopascal]. Once pellets were made, they were cured at temperatures ranging from 300-500° C. in a nitrogen gas environment. Before curing all pellets were soluble in concentrated sulfuric acid at room temperature, dissolving in less than 24 h. After curing, the samples exhibited lower solubility or were completely insoluble in concentrated sulfuric acid and boiling DMAc.

Pellet Preparation:

Processing conditions examples of ethynyl terminated m-PBI oligomers as described in pellet preparation are shown in Table 1.

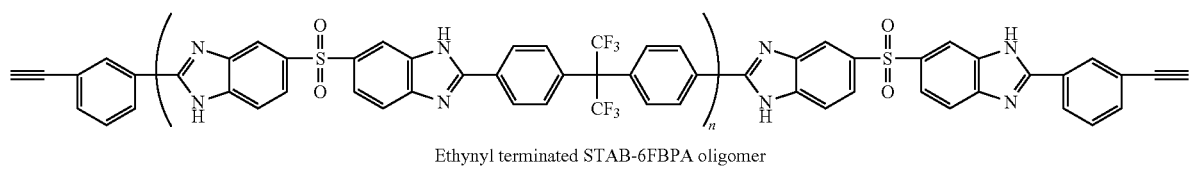

Ethynyl terminated STAB-6FBPA oligomer

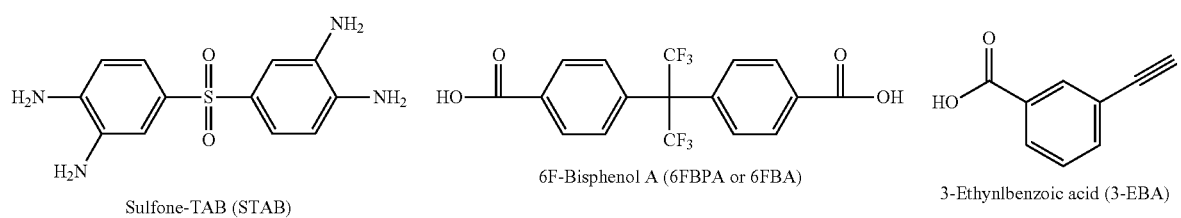

Sulfone-TAB (STAB)

6F-Bisphenol A (6FBPA or 6FBA)

3-Ethynlbenzoic acid (3-EBA)

TABLE 1

Preparation of pellets from ethynyl terminated m-PBI oligomers with 0.78" diameter at different temperatures and pressures.

| Pellet Example | Oligomer $M_n$ (Da) | Temperature (° C.) Pressure (kpsi) | Temperature (° C.) Pressure (kpsi) | Temperature (° C.) Pressure (kpsi) | Temperature (° C.) Pressure (kpsi) | Temperature (° C.) Pressure (kpsi) |
|---|---|---|---|---|---|---|
| 1 | 3,000 from Syn. Ex. 1 | 150 20 | 150 40 | 150 60 | 150 80 | — |
| 2 | 5,000 from Syn. Ex. 2 | 150 20 | 150 40 | 150 60 | 150 80 | 150 120 |
| 3 | 7,000 from Syn. Ex. 3 | 150 40 | 150 48 | 150 60 | 160 40 | 160 48 |

Processing conditions for STAB-based oligomers as described in pellet preparation are shown in Table 2. These pellets were made in a compression mold with a diameter of 0.5".

TABLE 2

Preparation of pellets from oligomers made from STAB and IPA with 0.5" diameter at different temperatures and pressures.

| Pellet Example | Oligomer Mn (Da) | Temperature (° C.) Pressure (ton) | Temperature (° C.) Pressure (ton) | Temperature (° C.) Pressure (ton) | Temperature (° C.) Pressure (ton) | Temperature (° C.) Pressure (ton) |
|---|---|---|---|---|---|---|
| 5 | 1,200 from Syn. Ex. 5 | 135 2.5 | 135 3 | 160 2.5 | 160 3 | 200 2.5 |
| 6 | 5,000 from Syn. Ex. 6 | 140 2.5 | 165 2.5 | 165 3 | 190 3 | — |

All the samples prepared in Tables 1 and 2 were readily broken with slight hand pressure and the fracture surface appeared friable and crumbly.

Mechanical Property Testing

Mechanical Example 1

Mechanical properties of a meta-ethynyl terminated m-PBI oligomer with a targeted molecular weight of 7,000 Da.

A meta-ethynyl m-PBI oligomer with a targeted molecular weight of 7,000 Da was made according to Syn. Ex. 3. The powder was loaded into a dog bone shaped mold and hot pressed at 160° C. for 3 hours using 10 tons of pressure. The molded dog bone was removed from the mold and subsequently cured at 450° C. in a nitrogen oven for 1 hour. The dog bone thickness was 1.86 mm. This material was tested using a mechanical testing machine and showed properties of stress at break of 63.5 MPa, elongation to break of 2.1%, and initial modulus of 3437 MPa.

Mechanical Example 2

Mechanical properties of a para-ethynyl terminated m-PBI oligomer with a targeted molecular weight of 7,000 Da.

A para-ethynyl m-PBI oligomer with a targeted molecular weight of 7,000 Da was made according to Syn. Ex. 3. The powder was loaded into a dog bone shaped mold and hot pressed at 160° C. for 3 hours using 10 tons of pressure. The molded dog bone was removed from the mold and subsequently cured at 450° C. in a nitrogen oven for 1 hour. The dog bone thickness was 2.04 mm. This material was tested using a mechanical testing machine and showed properties of stress at break of 36.5 MPa, elongation to break of 1.4%, and initial modulus of 2823 MPa.

Mechanical Example 3

Mechanical properties of a para-ethynyl terminated m-PBI oligomer with a targeted molecular weight of 10,000 Da.

A para-ethynyl m-PBI oligomer with a targeted molecular weight of 10,000 Da was made according to Syn. Ex. 4. The powder was loaded into a dog bone shaped mold and hot pressed at 160° C. for 3 hours using 10 tons of pressure. The molded dog bone was removed from the mold and subsequently cured at 450° C. in a nitrogen oven for 1 hour. The dog bone thickness was 2.25 mm. This material was tested using a mechanical testing machine and showed properties of stress at break of 77.0 MPa, elongation to break of 3.4%, and initial modulus of 2511 MPa.

Mechanical Example 4

Mechanical properties of a para-ethynyl terminated m-PBI oligomer with a targeted molecular weight of 15,000 Da.

A para-ethynyl m-PBI oligomer with a targeted molecular weight of 15,000 Da was made according to Syn. Ex. 4 using the following quantities of monomers to adjust the molecular weight: 10.7135 g TAB, 16.7535 g IBA, and 0.4906 g 4EHMS. The powder was loaded into a dog bone shaped mold and hot pressed at 160° C. for 3 hours using 10 tons of pressure. The molded dog bone was removed from the mold and subsequently cured at 450° C. in a nitrogen oven for 1 hour. The dog bone thickness was 2.54 mm. This material was tested using a mechanical testing machine and showed properties of stress at break of 43.4 MPa, elongation to break of 1.9%, and initial modulus of 2221 MPa.

Curing Studies and Solubility Tests

Cured Example 1

Pellets made from TAB-based oligomers described in Pellet Example 2 with Mn=5,000 Da were cured at 350° C. for 2 h. The sample was placed in sulfuric acid for 24 h and most of the sample remained undissolved.

Cured Example 2

Pellets made from TAB-based oligomers described in Pellet Example 2 with Mn=5,000 Da were cured at 450° C. for 1 h. This sample was placed in sulfuric acid for 24 h and was insoluble.

Cured Example 3

Pellets made from TAB-based oligomers described in Pellet Example 3 with Mn=7,000 Da were cured at 300° C. for 2 h. This sample was placed in sulfuric acid for 24 h and most of the sample remained undissolved.

Cured Example 4

Pellets made from TAB-based oligomers described in Pellet Example 3 with Mn=7,000 Da were cured at 400° C. for 2 h. This sample was placed in sulfuric acid for 24 h and most of the sample remained undissolved.

Cured Example 5

Pellets made from TAB-based oligomers described in Pellet Example 3 with Mn=7,000 Da were cured at 500° C. for 1 h. This sample was placed in sulfuric acid for 24 h and the sample remained undissolved.

Cured Example 6

Pellets made from TAB-based oligomers described in Pellet Example 3 with Mn=7,000 Da were cured at 500° C. for 2 h. This sample was insoluble in sulfuric acid after soaking for one week. In addition, the sample was shown to be insoluble when boiled in DMAc for four hrs.

Comparative Example

CELAZOLE U-60 products are made in a multi-step process. The raw material for U-60 is polybenzimidazole resin (high molecular weight, non end-group functionalized) that passes through a 100 mesh screen. The resin is thoroughly dried by heating to 160° C. for four hours in an inert environment. The dried resin, which is essentially free of water, is then placed in a molding tool where it will ultimately be subjected to intense heat (>420° C. for >8 hours).

Once the tool is properly filled, it is placed in a hydraulic press with heated platens. The press then begins to heat and pressurize the resin as part of a full production cycle that lasts eight hours. The production cycle includes brief degassing steps and ultimately results in the resin melting and flowing to create a consolidated plaque of pure polybenzimidazole that contains no voids or entrained gas. After the resin melts and assumes the shape of the tool the press is cooled which allows the resin to harden into a solid. The cooling and the pressure release are done gradually to prevent unduly shocking or stressing the shape.

After the plaque has fully cooled to ambient condition, it is heat treated (>10 hours at >300° C.) in an annealing step. The plaque is then typically cut into smaller shapes that allow specific parts to be machined, one at a time. Machining polybenzimidazole parts requires diamond tipped tools and longer cutting cycle time because of the high hardness of U-60 plaques.

Two dog bone bars included in this description were produced by the method outlined above. The dog bones were tested under identical conditions and using the same instrument as the examples above. The two bars showed stress at break of 52.6 MPa and 67.4 MPa, and elongation-to-break of 2.6% and 3.5%.

Inherent Viscosity (IV) Measurement Method 0.050 g polybenzimidazole is added to a 25 mL volumetric flask. The flask is filled with concentrated sulfuric acid for a final concentration of 0.2 g/dL. The flask is shaken on a mechanical shaker until all polybenzimidazole is dissolved. The polybenzimidazole solution is filtered through a 0.45 μm PTFE syringe filter and added to a 200 μm Ubbelohde viscometer. The viscometer is placed into a 23.0° C. water bath and allowed to equilibrate for 30 minutes. Measurements are recorded until three consecutive times are within 0.1 seconds. The average of these three times is used to calculate the inherent viscosity using the following equation:

$$\eta_{inh} = \frac{\ln(t/t_0)}{C}$$

$\eta_{inh}$ (dL/g): inherent viscosity (IV)
t (sec): solution flow time
$t_0$ (sec): solvent flow time (96% sulfuric acid)
C (g/d L): solution concentration.

Mechanical Property Measurement Method

Mechanical Properties were Measured According to ASTM D638.

The present invention may be embodied in other forms without departing from the spirit and the essential attributes thereof, and, accordingly, reference should be made to the appended claims, rather than to the foregoing specification, as indicating the scope of the invention.

We claim:

1. A polybenzimidazole (PBI) resin comprises: a polybenzimidazole oligomer with a molecular weight in the IV range of about 0.015-0.60 dL/g or about 1000 to 15,000 Daltons (Da) and the oligomer has at least two reactive end groups.

2. The PBI resin of claim 1 wherein the polybenzimidazole oligomer is the reaction product of a tetraamine, a dicarboxylic component, and a reactive end group moiety.

3. The PBI resin of claim 2 wherein the reactive end group has an alkynyl and/or a cyclobutene group.

4. The PBI resin of claim 1 further comprising one or more additives selected from the group consisting of fillers, flame retardants, flame retardant aids, plasticizers, antioxidants, releasing agents, light fastness agents, weathering agents, colorants, pigments, modifiers, antistatic agents, hydrolysis inhibitors, and reinforcing agents.

5. A method of making a polybenzimidazole oligomer with at least two reactive end groups comprising the steps of:
   reacting a tetraamine, a dicarboxylic component, and a reactive end group moiety in a solvent at a temperature greater than room temperature for a period of time;
   precipitating the oligomer with a molecular weight in the IV range of about 0.015-0.60 dL/g or about 1000 to 15,000 Daltons (Da) from the solvent after reacting; and
   removing any reaction by-products from the oligomer after precipitating.

6. The method of claim 5 wherein the reactive end group has an alkynyl and/or a cyclobutene group.

7. A method of making a molded polybenzimidazole (PBI) comprising the steps of:
   molding a polybenzimidazole oligomer with a molecular weight in the IV range of about 0.015-0.60 dL/g or about 1000 to 15,000 Daltons (Da) and the oligomer has at least two reactive end groups,
   curing the molded oligomer at a temperature sufficient to react the end groups, and
   rendering the molded PBI article.

8. The method of claim 7 wherein the reactive end group has an alkynyl and/or a cyclobutene group.

9. The method of claim 7 wherein the polybenzimidazole oligomer with at least two reactive end groups further includes one or more additives selected from the group consisting of fillers, flame retardants, flame retardant aids, plasticizers, antioxidants, releasing agents, light fastness agents, weathering agents, colorants, pigments, modifiers, antistatic agents, hydrolysis inhibitors, and reinforcing agents.

10. A polybenzimidazole (PBI) molded article comprises:
    a polymer cured from a polybenzimidazole oligomer with a molecular weight in the IV range of about 0.015-0.60 dL/g or about 1000 to 15,000 Daltons (Da) and the oligomer has with at least two reactive end groups.

11. The article of claim 10 wherein the reactive end group has an alkynyl and/or a cyclobutene group.

12. The article of claim 10 further comprising one or more additives selected from the group consisting of fillers, flame retardants, flame retardant aids, plasticizers, antioxidants, releasing agents, light fastness agents, weathering agents, colorants, pigments, modifiers, antistatic agents, hydrolysis inhibitors, and reinforcing agents.

* * * * *